United States Patent
Conway et al.

(10) Patent No.: US 11,737,860 B2
(45) Date of Patent: *Aug. 29, 2023

(54) DEVICE FOR CONTROLLING FECAL INCONTINENCE

(71) Applicant: Minnesota Medical Technologies, Stewartville, MN (US)

(72) Inventors: Anthony J. Conway, Chatfield, MN (US); Sarah L. Grinde, Spring Grove, MN (US); Philip J. Conway, Chatfield, MN (US); Adil Bharucha, Rochester, MN (US)

(73) Assignee: Minnesota Medical Technologies, Stewartville, MN (US)

( * ) Notice: Subject to any disclaimer, the term of this patent is extended or adjusted under 35 U.S.C. 154(b) by 243 days.

This patent is subject to a terminal disclaimer.

(21) Appl. No.: 17/183,185

(22) Filed: Feb. 23, 2021

(65) Prior Publication Data

US 2021/0177565 A1 Jun. 17, 2021

Related U.S. Application Data (63) Continuation of application No. 15/281,232, filed on Sep. 30, 2016, now Pat. No. 10,959,822.

(60) Provisional application No. 62/239,397, filed on Oct. 9, 2015.

(51) Int. Cl.
*A61F 2/00* (2006.01)

(52) U.S. Cl.
CPC .......... *A61F 2/0009* (2013.01); *A61F 2/0004* (2013.01)

(58) Field of Classification Search
CPC ................ A61F 2/0009; A61F 13/2011; A61F 2013/1513
See application file for complete search history.

(56) References Cited

U.S. PATENT DOCUMENTS

| | | | |
|---|---|---|---|
| 2,499,045 A * | 2/1950 | Walker | A61M 29/02 606/192 |
| 4,686,985 A | 8/1987 | Lottick | |
| 4,813,422 A | 3/1989 | Fisher et al. | |
| 5,593,443 A | 6/1997 | Carter | |
| 5,782,745 A | 7/1998 | Benderev | |
| 5,817,124 A | 10/1998 | Karell | |
| 5,906,575 A | 5/1999 | Conway | |
| 6,096,057 A | 8/2000 | Klingenstein | |
| 7,553,273 B2 | 6/2009 | Ferguson | |
| 8,449,448 B2 | 5/2013 | Shalon et al. | |
| 10,959,822 B2 * | 3/2021 | Conway | A61F 2/0004 |
| 2005/0038380 A1 | 2/2005 | Nemir et al. | |
| 2007/0282161 A1 | 12/2007 | Ferguson et al. | |

FOREIGN PATENT DOCUMENTS

| | | |
|---|---|---|
| WO | 0003659 A1 | 1/2000 |
| WO | 2011063243 A1 | 5/2011 |

OTHER PUBLICATIONS

European Patent Office, Extended Search Report for Application No. 16193036.7 dated Apr. 19, 2017, 9 pages.

* cited by examiner

*Primary Examiner* — Samuel G Gilbert
(74) *Attorney, Agent, or Firm* — Merchant & Gould P.C.

(57) ABSTRACT

The present invention relates to devices for treating or managing fecal or bowel incontinence and methods employing them. Such a device can form a seal with at least a portion of the bowel to prevent unwanted discharge of fecal matter from the rectum.

19 Claims, 6 Drawing Sheets

FIG. 6A

DEVICE FOR CONTROLLING FECAL INCONTINENCE

CROSS-REFERENCE TO RELATED APPLICATIONS

This application is a continuation of U.S. application Ser. No. 15/281,232, entitled "DEVICE FOR CONTROLLING FECAL INCONTINENCE," filed on Sep. 30, 2016, now U.S. Pat. No. 10,959,822, which claims priority to U.S. Provisional Application No. 62/239,397, entitled "DEVICE FOR CONTROLLING FECAL INCONTINENCE," filed on Oct. 9, 2015, the disclosures of which are hereby incorporated by reference in their entireties.

FIELD OF THE INVENTION

The present invention relates to devices for treating or managing fecal or bowel incontinence and methods employing them. In an embodiment, such a device can form a seal with at least a portion of the bowel to prevent unwanted discharge of fecal matter from the rectum.

BACKGROUND OF THE INVENTION

Fecal incontinence is a physically and psychologically debilitating disease affecting an estimated 1-2% of the general population living independently and nearly 40-50% of those living in long term care facilities. While the condition affects men and women alike, it is more prevalent in women, in the elderly, and in nursing home patients. Whether living independently or institutionalized, the effects of fecal incontinence can cause significant psychological damage as well as consume significant health care resources.

People living with fecal incontinence are often embarrassed due to the social stigma attached to the affliction. This not only leads to delayed treatment, but not surprisingly, to damaging psychological issues which may include self-imposed social isolation, severe depression, personal and family strains, and increased anxiety. The very real problem of social isolation can have a significant effect on persons suffering from fecal incontinence resulting in a detrimental impact on their quality of life. For example, many people with this condition will refrain from going out in public or interacting with friends and loved ones leading to a sedentary lifestyle and loss of meaningful relationships and/or intimacy.

Further, the cost of care for treating and/or managing the condition for patients who are institutionalized is significant not only in regard to the personnel resources required, but also due to increased risk of infection, bed sores, and even increases in the length of stay for temporarily institutionalized patients. Fecal incontinence is often cited as one of the leading causes of permanent institutionalization.

Fecal or bowel incontinence is the inability to control the discharge of fecal matter through the rectum. There are three clinical subtypes related to fecal incontinence; 1) passive incontinence—an involuntary discharge of stool or gas without awareness, 2) urge incontinence—the discharge of fecal matter in spite of active attempts to retain bowel contents, and 3) fecal seepage—the leakage of stool following otherwise normal evacuation.

At the end, the human bowel includes a system that regulates the expulsion of fecal matter or feces. The fecal control system includes three functional portions, the Houston valve (or flap) region, the rectal bladder neck, and two sphincters, internal and external. The sphincters are the outermost portion of the control system. The rectal bladder neck is adjacent the sphincter area and above or internal to the sphincters. The Houston valves or flaps are above or internal to the rectal bladder neck. The Houston valves or flaps are believed to act to modulate or slow the descent of fecal matter so that it does not immediately descend into the rectum and toward the rectal neck. Most humans have three Houston valves or flaps.

Age or disease can result in one or more problems that can cause a loss of function and fecal incontinence. For example, one or both of the anal sphincters can lose the ability to seal. They can become weak or distended often to the point where the canal remains open—defined as a Patulous Anal Canal. The rectal neck can weaken and become distended or loose. One or more of the Houston valves or flaps can weaken or reduce their function.

Generally, the treatment of fecal incontinence is divided into two categories; conservative management and surgical intervention. Current treatment options include products such as: diaper or absorbents, electrical neuro stimulation, bulking agents, plugs, artificial sphincters, collection kits, and pessaries. The most common treatment option for both men and women, whether in a facility or living independently, are absorbents. These products are bulky, inconvenient, and may result in embarrassing situations for the user if not attended properly. Further, use of these products can increase the likelihood of infection and bed sores while requiring a large amount of resources to change, clean, and reapply the product, to say nothing of dealing with the significant odor problems and the indignities that relate to that issue.

Other options for patients are more invasive such as sphincter repair, the use of artificial sphincters, injectable bulking agents, neuro stimulation, and collection kits. These options are usually reserved for those who have more severe fecal incontinence issues.

Current products and treatment methods are inadequate and do not address the negative impact on a person's quality of life or risk of infection. There remains a need for devices and methods to effectively treat fecal incontinence.

SUMMARY OF THE INVENTION

The present invention relates to devices for treating or managing fecal or bowel incontinence and methods employing them. In an embodiment, such a device can form a seal with at least a portion of the bowel to prevent unwanted discharge of fecal matter from the rectum.

The present invention includes a fecal incontinence control device including a sphincter support. The sphincter support can be configured to conform to and support an external anal sphincter, an internal anal sphincter, or both the external and internal anal sphincters. The sphincter support can be configured to be encircled by the anal sphincters when inserted in the subject. The sphincter support can be configured to be self retaining near the anal sphincters.

The fecal incontinence control device can also include a rectal neck support. The fecal incontinence control device can also include a Houston valve support. The fecal incontinence control device can also include a rectal neck support and a Houston valve support.

The present invention relates to a device including an external body around an internal body. The external body can be configured to conform to and support a subject's anal sphincter(s). This device can also include a second body. The second body can be configured to seal a rectal neck. This device can also include a third body. The third body can be configured to support a Houston valve. The device can include the external body, the internal body and the second body. The device can include the external body, the internal body and the third body. The device can include the external body, the internal body, the second body, and the third body.

The present invention includes a method of treating or managing fecal incontinence. This method includes inserting the present device into (the anal canal and/or rectum of) a subject suffering from fecal incontinence. The present invention can include a kit including the present device along with packaging and instructions for use. The present invention also relates to a device including a sphincteral prosthesis configured for treating or managing fecal incontinence.

DETAILED DESCRIPTION OF THE INVENTION

The present invention relates to a device for stopping, treating, or reducing fecal incontinence. The device provides advantages not found in existing devices for addressing this malady. The device can be comfortable during and after insertion. It can be easier to use for either a care giver or the subject themselves. The device can be disposable. And, it can be removed either manually prior to a bowel movement or it can come out as part of the bowel movement. The device can be a self-retaining disposable anal insert.

The present device can be a soft and deformable self-retaining assist for one, two, or all three of the major functional areas of the rectal fecal control system. The three functional areas are: 1) the internal and external sphincter control system in the rectum; 2) the rectal bladder neck, which resides just above the sphincter area; and 3) the Houston Valve configuration or portion of the rectum.

This device can be viewed as including or serving as a sphincteral prosthesis. For example, in an embodiment, the device can provide a soft, deformable substrate against which one or both of the sphincters can depress and form a seal which has otherwise been lost due to age, disease, or the like. Although not limiting to the present invention, it is believed that the device allows leaky, weak, or impaired sphincters to seal around a soft and deformable portion of the insert that is encircled by the sphincter muscles, which can result in the subject regaining control over the anal canal. In an embodiment, the device provides a soft, pliable, generally cylindrical substrate along which the sphincter muscles can compress to form an improved seal for prevention of fecal leakage. This portion of the device can be made up of or include a cylinder of fluid encased within a thin, deformable elastomeric skin.

In an embodiment, the device can provide support in the rectal neck, which can, for example, diffuse pressure and provide an additional seal above the sphincter(s). Such an embodiment can support the entire rectal neck area. For example, the device can include a soft, comfortable, generally annular fluid chamber that can seat against and gently seal the rectal neck. Such a seal can distribute pressure evenly around the area funneling fecal matter into the anal canal. In an embodiment, the device includes a soft, pliable, bulbous portion which conformably seats in the rectal neck. This embodiment can provide an improved seal to protect against fecal leakage. This portion of the device can be made up of or include a cylinder of fluid encased within a thin, deformable elastomeric skin.

For example, in an embodiment, the device can provide what can be considered an additional Houston valve or flap. Such an embodiment can be envisioned as providing an assist or additional blockage to the Houston Valve(s) or flap(s) which may have been weakened by age or disease. Such a device can include a soft, fluid filled chamber which seats in the Houston Valve region. Such a chamber can aid their function of modulating the rate of descent of fecal matter. In an embodiment, the device includes a wider soft, pliable, generally cylindrical portion providing additional blockage against fecal descent in the general area of the rectal Houston Valves (flaps). This portion of the device can be made up of or include a cylinder of fluid encased within a thin, deformable elastomeric skin.

The device can also include a handle, for example, a broad stopper portion, at the exterior end which prevents over insertion and provides for proper positioning of the device within the rectum.

In an embodiment, the device can be expelled from the user during a bowel movement. This can be envisioned as a process in which, during the bowel movement, when the sphincters relax and open, the fluid in a bulbous neck chamber is gently forced downward into and through the expanding outer sphincteral area. This shrinks the rectal neck portion of the device within the sphincters allowing the entire device to be passed out of the body along with expelled fecal matter. Alternately, the patient or caregiver can simply pro-actively remove the device in order to encourage or facilitate the onset of fecal expulsion.

In an embodiment, the present device is a self-retaining anal insert. It can be configured to support weakened or damaged sphincter muscles to help them seal a distended, loose, or patulous anal canal. This embodiment can include a portion residing in the anal canal that is conformable or deformable under the pressure of the sphincter muscles, helping them to seal the anal canal from unwanted leakage.

Embodiments of the Present Device and Methods

A. In certain embodiments, the present fecal incontinence treatment device includes one or more of a sphincter support, a rectal neck support, and a Houston valve support.

The device can include a sphincter support. The sphincter support can be sufficiently conformable or pliable that pressure from one or both anal sphincters causes the support to conform to the shape of the tissue of the sphincter or near the sphincter(s). That is, the sphincter support can be configured to conform to and support a subject's anal sphincter(s). This can provide a seal that assists in retaining fecal matter within the subject rather than allowing it to leak from the subject with the result of fecal incontinence. The sphincter support can be in the form of an external body around an internal body. The sphincter support can be in the form of a single (first) body.

The sphincter support can conform to the subject's anal sphincter(s) or nearby tissue and also push back against the tissue to provide a seal. The sphincter support does not completely collapse under the pressure of the sphincter(s), provides a seal, and can be retained within the subject's anal canal. The sphincter support can be configured to conform to and support an external anal sphincter, an internal anal sphincter, or both the external and internal anal sphincters. The sphincter support can be configured to be encircled by the anal sphincters when inserted in the subject. The sphincter support can be configured to be self retaining near the anal sphincters.

In an embodiment, the present device includes a rectal neck support. The rectal neck support can be configured to be positioned in or near the rectal neck. The rectal neck support can be configured to provide a seal at or near the rectal neck. In an embodiment, the rectal neck support can be generally ring shaped. The rectal neck support can have a generally toroid configuration. The rectal neck support can have a generally annular configuration. In an embodiment, the rectal neck support has a bulbous configuration. The rectal neck support can be in the form of a second body.

The rectal neck support can be coupled to the sphincter support. In such an embodiment, a deformable substance of the rectal neck support body can be in fluid communication with the deformable substance of the sphincter support. For example, a single deformable substance can include the substance of the rectal neck support and the substance of the sphincter support.

In an embodiment, the present device includes a Houston valve support. The Houston valve support can be configured to be positioned near or contacting one or more of the Houston valves (in the rectum) when inserted in a subject. The Houston valve support can be configured to provide a seal at or near the Houston valve(s). The Houston valve support can be in the form of a third body.

In an embodiment, the Houston valve support includes a generally cylindrical portion and a generally ring-shaped (e.g., annular or toroid) portion, the generally ring-shaped portion at an end distal to the external deformable body. In an embodiment, the Houston valve support includes a generally cylindrical portion and a generally ring-shaped portion, the generally ring-shaped portion at an end distal to the sphincter support. In an embodiment, the Houston valve support includes a generally cylindrical portion and a generally bulbous portion, the generally bulbous portion at an end distal to the sphincter support.

In an embodiment, the present device includes a sphincter support and a rectal neck support. In an embodiment, the present device includes a sphincter support and a Houston valve support. In an embodiment, the present device includes a sphincter support, a rectal neck support, and a Houston valve support; rectal neck support being disposed between the sphincter support and the Houston valve support.

These embodiments can also include at one end the handle, as described above.

In an embodiment, the present device includes a shaft. The shaft can run axially through the support(s). In an embodiment, the sphincter support can be radially disposed around the shaft. In an embodiment, the device can include a rectal neck support radially disposed around the shaft. In an embodiment, the device can include a Houston valve support radially disposed around the shaft.

In an embodiment, the present device includes the axial shaft and the sphincter support. In an embodiment, the present device includes the axial shaft, the sphincter support, and the rectal neck support. In an embodiment, the present device includes the axial shaft, the sphincter support, and the Houston valve support. In an embodiment, the present device includes the axial shaft, the sphincter support, the rectal neck support, and the Houston valve support.

The present device can also include an applicator that occupies the axial shaft. The applicator can be in the form of a rigid or nearly rigid rod that can be useful for inserting the present device through the anus and into the subject. In an embodiment, the applicator will be assembled with the device so that the tip of the shaft of the device is seated on the tip of the applicator and the external retainer of the device is seated against the wider portion of the applicator handle.

These embodiments can also include the tip as described below.

The surface of the support(s) can be lubricated or lubricious. Suitable lubricants include those described below. The support(s) can include a resilient deformable shell as described below. The support(s) can include a deformable substance as described below. The support(s) can include a deformation resistant substance as described below.

B. In certain embodiments, the present device includes one, two, three, or four bodies.

The device includes an external body around an internal body. The external body is sufficiently conformable or pliable that pressure from a body part, such as an anal sphincter, causes the external body to conform to the shape of the tissue of the sphincter(s) or near the sphincter(s). That is, the external body can be configured to conform to and support a subject's anal sphincter(s). This can provide a seal that assists in retaining fecal matter within the subject rather than allowing it to leak from the subject with the result of fecal incontinence. Each body can be in the form of a resilient deformable shell containing a deformable substance. In an embodiment, the external body has a generally cylindrical configuration.

The internal body supports the external body. The conformable body conforms to the subject's interior (e.g., anal sphincter(s) or other tissue) and the internal body provides sufficient support that the device can push back against the tissue to provide a seal. The device does not completely collapse under the pressure of the sphincter(s), provides a seal, and can be retained within the subject's anal canal. The internal body can be within the external body, but need not be completely surrounded by that body.

For example, the external body can be positioned to be between the internal body and the subject's tissue (when the device is inserted). But, the external body need not cover those portions of the internal body that would not contact the subject's tissue. The internal body can reside within the external body. The internal body can be in the form of a resilient deformable shell filled with a deformable substance. The deformable substance in the inner body can be denser or less deformable than the deformable substance within the external body. In an embodiment, the internal body has a generally cylindrical configuration.

The internal body can be more dimensionally stable (e.g., less conformable) than the outer body. Such a body can be considered a stable internal body. The internal body can be in the form of a resilient deformable shell filled with a deformation resisting substance. A deformation resisting substance can be denser or less deformable than a deformable sub stance.

The device can be configured to conform to and support an external anal sphincter, an internal anal sphincter, or both the external and internal anal sphincters. This embodiment can be configured to be encircled by the anal sphincters when inserted in the subject. This embodiment can be configured to be self retaining near the anal sphincters. This embodiment can be configured to be expelled from the subject with a bowel movement.

In an embodiment, the present device includes a second body. The second body can be configured to be positioned in or near the rectal neck. The rectal neck is that portion of the anal canal just above (more distant from the anus than) the anal sphincters. The anal canal widens in the area of the rectal neck. The second body can be configured to provide a seal at or near the rectal neck. The second body can include a resilient deformable shell retaining a deformable substance.

In an embodiment, the second body can be generally ring shaped. The second body can have a generally ring shaped configuration. The second body can have a generally toroid configuration. The second body can have a generally annular configuration. In an embodiment, the second body has a generally bulbous configuration.

The second body can be coupled to the external body. In such an embodiment, the deformable substance of the second body can be in fluid communication with the deformable substance of the external body. For example, a single deformable substance can include the substance of the second body and the substance of the external body.

In an embodiment, the present device includes a third body. The third body can be configured to be positioned near or contacting one or more of the Houston valves (in the rectum) when inserted in a subject. The third body can be envisioned as providing or can be configured to provide support to the Houston valve(s). The third body can be configured to provide a seal at or near the Houston valve(s). The third body can include a resilient deformable shell retaining a deformable substance.

In an embodiment, the third body includes a generally cylindrical portion and a generally ring-shaped (e.g., annular or toroid) portion, the generally ring-shaped portion at an end distal to the external deformable body. In an embodiment, the third body includes a generally cylindrical portion and a generally ring-shaped portion, the generally ring-shaped portion at an end distal to the external deformable body. In an embodiment, the third body includes a generally cylindrical portion and a generally bulbous portion, the generally bulbous portion at an end distal to the external deformable body.

In an embodiment, the present device includes an external body around an internal body and a second body. In an embodiment, the present device includes an external body around an internal body and a third body. In an embodiment, the present device includes an external body around an internal body, a second body, and a third body; the second body being disposed between the external body and the third body.

In an embodiment, the present device includes at one end a handle. The handle can be envisioned as a stop that can provide proper positioning of the device within the subject (e.g., the subject's anal canal, rectum, anal neck, or the like). The handle can prevent over-insertion of the device. The handle can also provide a portion of the device that can be gripped when inserting or removing the device.

In an embodiment, the present device includes a shaft. The shaft can run axially through the conformable body(ies) and the internal body. In an embodiment, the stable body can be radially disposed around the shaft and the external body radially disposed around the shaft and the stable body. In an embodiment, the device can include a second body radially disposed around the shaft. In an embodiment, the device can include a third body radially disposed around the shaft. In an embodiment, the shaft includes a member that is present during insertion of the device and can be removed after insertion.

In an embodiment, the present device includes the axial shaft, the external body, and the internal body. In an embodiment, the present device includes the axial shaft, the external body, the internal body, and the second body. In an embodiment, the present device includes the axial shaft, the external body, the internal body, and the third body. In an embodiment, the present device includes the axial shaft, the external body, the internal body, the second body, and the third body.

The device can also include a tip. The tip can be at the end of the device that first enters the subject. The tip can be smaller (e.g., smaller diameter) than the conformable body(ies), resilient, and ease entry of the device through the anus and into the anal canal and rectum. These embodiments of the present device can also include an applicator, as described above.

The surface of the device can be lubricated or lubricious. Suitable lubricants include mineral oil, petrolatum, glycerin, polyethylene glycol, propylene glycol, or the like, or another lubricant used for inserting devices through the anus. In an embodiment the deformable shell can be made from a lubricious polymer.

In an embodiment, the resilient deformable shell includes silicone rubber, latex, kraton, or another resilient polymer employed in anal inserts.

In an embodiment, the deformable substance includes a fluid or gel, such as petrolatum, mineral oil, glycerin, closed cell foam, or the like. In an embodiment, the deformable substance comprises petrolatum, mineral oil, or a mixture thereof. In an embodiment, the deformable substance is selected from the group consisting of petrolatum, mineral oil, and a mixture thereof.

In an embodiment, the deformation resistant substance includes petrolatum or petrolatum mixed with a lower proportion of mineral oil than the deformable substance employed in the embodiment.

In an embodiment, the one or more bodies making up the device can each be made of closed cell foam.

C. The present invention includes methods and kits employing or including the present device.

In an embodiment, the present invention includes a method of treating or managing fecal incontinence. This method can include inserting the present device through the anus of a subject suffering from fecal incontinence. The device can be inserted so that it seals at the anal sphincter(s), the rectal neck, the Houston valves, or at more than one of these anatomical features. The method can include manually removing the device to allow the subject to expel fecal matter. The method can include expelling the device from the subject by initiating a bowel movement.

Subjects suffering from fecal incontinence can suffer from a leaky anal sphincter, a weak anal sphincter, or an otherwise impaired anal sphincter, which can result in a patulous anal canal.

In an embodiment, the present invention includes a system or kit. The system or kit can be used for treating or managing fecal incontinence. The system or kit can include the present device and one or more of lubricant, gloves, drape, tissues, sterilization materials, or the like. The components of the system or kit can be enclosed within a sterile package.

D. Making the present devices.

The present devices can be made by any of a variety of suitable methods for making medical devices, such as urinary catheters. Suitable methods include those disclosed in U.S. Pat. Nos. 6,626,888; 6,479,000; 5,981,954; the disclosures of which are incorporated herein by reference.

E. The present invention includes illustrated embodiments of the present device.

FIGS. 2A through 2D schematically illustrate embodiments of the present device including a sphincteral prosthesis 1, a rectal neck prosthesis 3, a Houston valve prosthesis 5, and optional grip stop 7. In these Figures, optional grip stop 7 is at the end of the device nearest the anus. In fact, optional grip stop 7 would remain outside the anus and can be used in inserting and removing this embodiment of the device.

Figure 1:
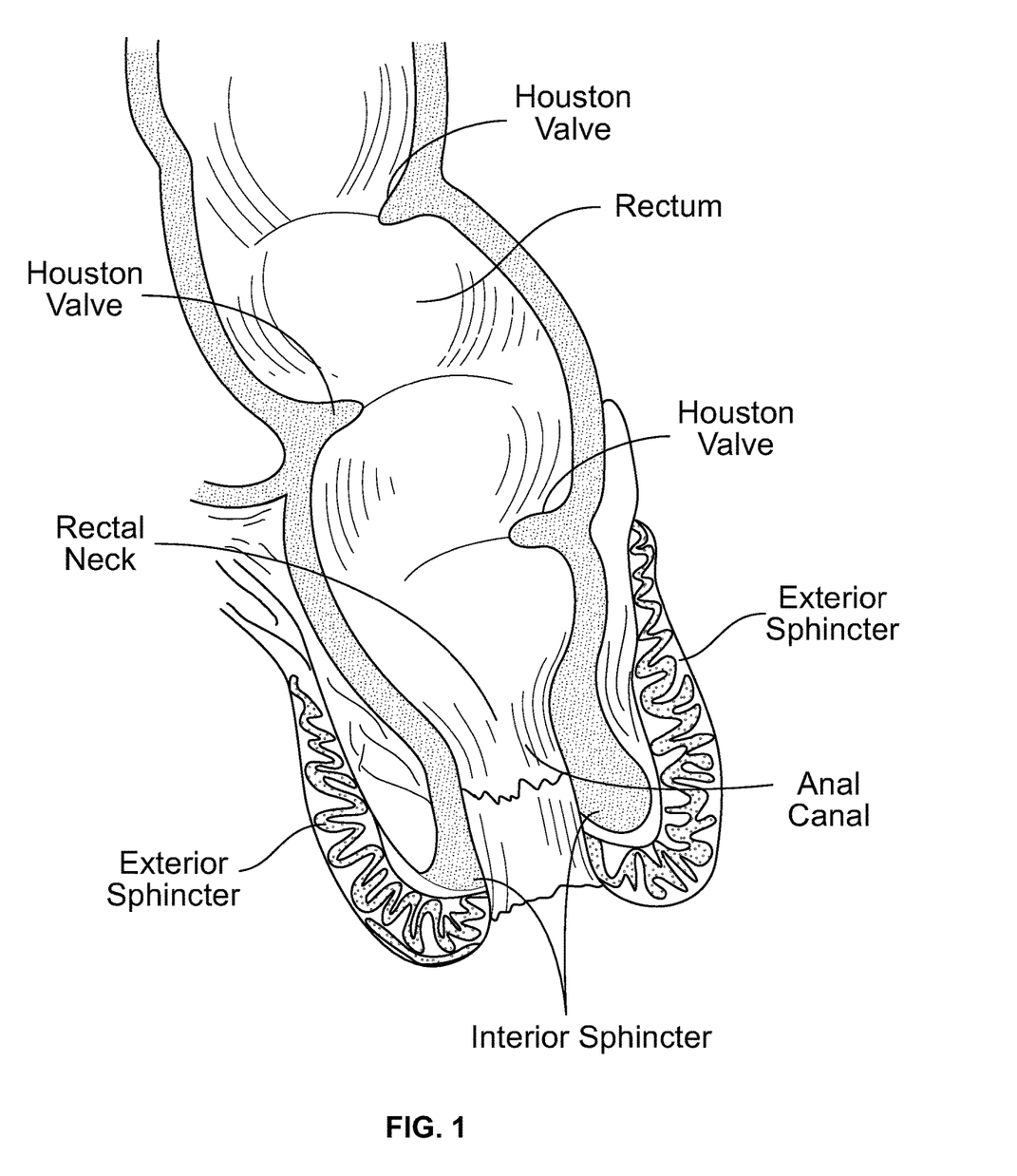
FIG. 1 schematically illustrates the rectum and anal canal regions of the digestive tract.
Figure 2A:
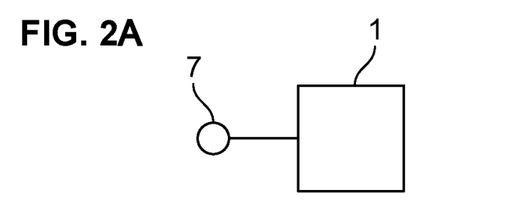
FIG. 2A schematically illustrates an embodiment of the present device.

Sphincteral prosthesis 1 is configured to remain adjacent to or in contact with the anal sphincter(s) to form a seal that can reduce or prevent leakage of fecal matter, thus treating or managing fecal incontinence. Sphincteral prosthesis 1 can include a soft, deformable substrate against which the sphincter(s) can depress and form a seal. In an embodiment, impaired sphincters can seal around a soft and deformable portion of this prosthesis. The prosthesis can take the form of a soft, pliable, generally cylindrical substrate along which the sphincter muscles can compress. Pressure from the anal sphincter(s) can cause the sphincteral prosthesis to conform to the shape of the tissue of the sphincter or near the sphincter(s). The sphincteral prosthesis can conform to and support a subject's anal sphincter(s). FIG. 2A schematically illustrates an embodiment of the present device including sphincteral prosthesis 1 without the other prostheses.

In certain embodiments, sphincteral prosthesis 1 is in the form of the sphincter support or the external body around an internal body.

Figure 2B:
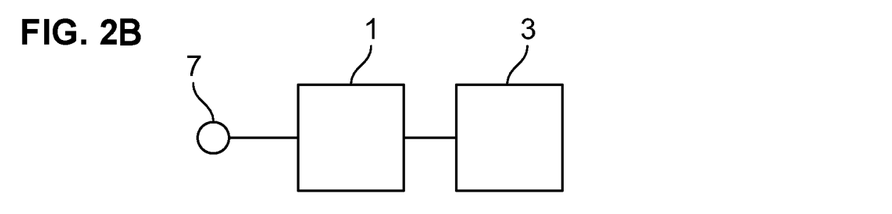
FIG. 2B schematically illustrates an embodiment of the present device.
Figure 2C:
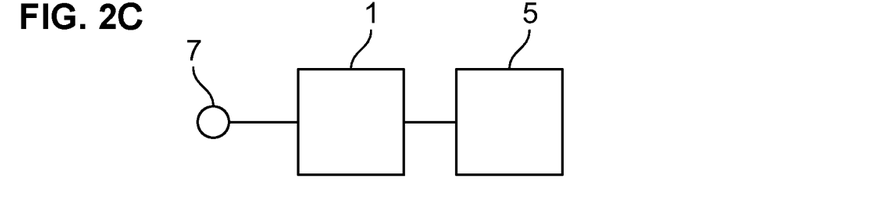
FIG. 2C schematically illustrates an embodiment of the present device.
Figure 2D:
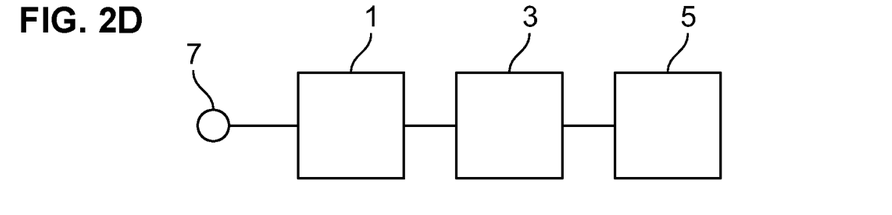
FIG. 2D schematically illustrates an embodiment of the present device.

Rectal neck prosthesis 3 can be configured to seat in and contact the rectal neck to form a seal that can reduce or prevent leakage of fecal matter, thus treating or managing fecal incontinence. FIGS. 2B and 2D schematically illustrate embodiments of the present device including rectal neck prosthesis 3.

Rectal neck prosthesis 3 can be employed in conjunction with sphincteral prosthesis 1 to treat or manage fecal incontinence. In an embodiment, rectal neck prosthesis 3 can diffuse pressure and provide an additional seal above the sphincter(s). Rectal neck prosthesis 3 can include a soft, comfortable, generally annular fluid chamber that can seat against and gently seal the rectal neck. Rectal neck prosthesis 3 can include a soft, pliable, bulbous portion which conformably seats in the rectal neck. Rectal neck prosthesis 3 can be coupled to the sphincteral prosthesis, for example, to form a unitary body.

In certain embodiments, rectal neck prosthesis 1 is in the form of the rectal neck support or the second body.

Houston valve prosthesis 5 can be configured to seat in and contact the region of the Houston valves to form a seal that can reduce or prevent leakage of fecal matter, thus treating or managing fecal incontinence. FIGS. 2C and 2D schematically illustrate embodiments of the present device including Houston valve prosthesis 5.

Houston valve prosthesis 5 can be employed in conjunction with sphincteral prosthesis 1 to treat or manage fecal incontinence. In an embodiment, Houston valve prosthesis 5 can provide what can be considered an additional and Houston valve or flap. Such a Houston valve prosthesis 5 can be envisioned as providing an assist or additional blockage to the Houston Valve(s) or flap(s). Houston valve prosthesis 5 can seat in the Houston Valve region. Houston valve prosthesis 5 can assist in modulating the rate of descent of fecal matter. Houston valve prosthesis 5 can be configured to be positioned near or contacting one or more of the Houston valves (in the rectum) when inserted in a subject. Houston valve prosthesis 5 can provide support to the Houston valve(s). Houston valve prosthesis 5 can be configured to provide a seal at or near the Houston valve(s).

In certain embodiments, Houston valve prosthesis 5 is in the form of the Houston valve support or the third body.

Figure 3A:
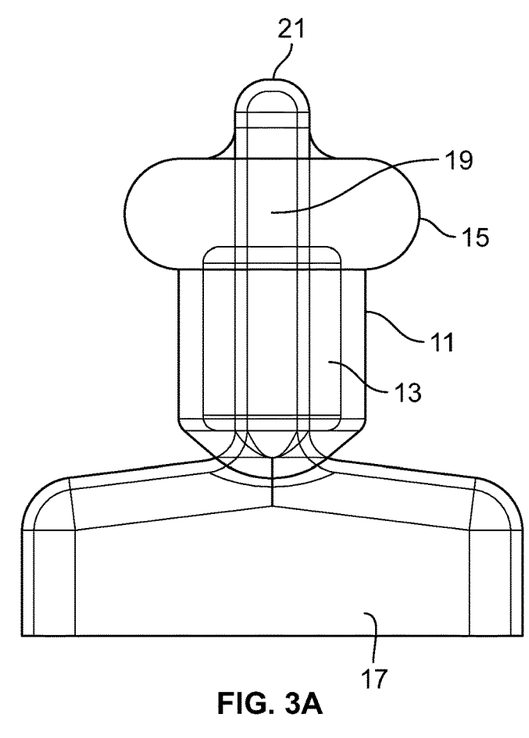
FIG. 3A schematically illustrates an embodiment of the present device.
Figure 3B:
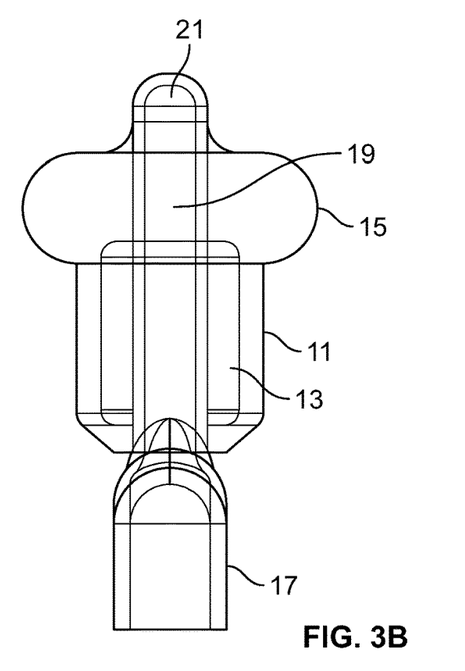
FIG. 3B schematically illustrates an embodiment of the present device.

FIGS. 3A and 3B schematically illustrate an embodiment of the present device including outer column 11, inner column 13, first bulb 15, grip 17, stem 19, and apex 21.

Outer column 11 is a resilient structure that can, when the device is inserted in a subject, be positioned near the anal sphincter(s) to provide a seal that reduces or eliminates leakage of fecal matter, thus treating or managing fecal incontinence. Outer column 11 can be made of a soft, deformable material against which one or both of the sphincters can depress and form a seal. Outer column 11 can be a soft and deformable portion of the device that is encircled by the sphincter muscles. In an embodiment, outer column 11 can provide a soft, pliable, generally cylindrical substrate along which the sphincter muscles can compress to form a seal for prevention of fecal leakage. This portion of the device can be made up of or include a cylinder of fluid encased within a thin, deformable elastomeric skin. Outer column 11 can be sufficiently conformable or pliable that pressure from anal sphincter(s) can cause it to conform to the shape of the tissue of the sphincter(s) or near the sphincter(s). Outer column 11 can be configured to conform to and support a subject's anal sphincter(s).

In an embodiment, the external body described above can take the form of outer column 11.

Inner column 13 is disposed between outer column 11 and stem 19. Inner column 13 can be configured to provide support to outer column 11, so that the device does not collapse under pressure from the anal sphincter(s). Inner column 13 can be less resilient than outer column 11. Inner column 13 can provide sufficient support that the device can push back against the sphincter tissue to provide a seal and allow the device to be retained within the subject's anal canal.

In an embodiment, the internal body described above can take the form of inner column 13. In an embodiment, the sphincter support described above can take the form of the structures of outer column 11 and inner column 13.

First bulb 15 is a resilient structure that can, when the device is inserted in a subject, be positioned near the rectal neck (a widening in the anal canal) to provide an additional seal that reduces or eliminates leakage of fecal matter, thus treating or managing fecal incontinence. In an embodiment, first bulb 15 can seat in the rectal neck, diffuse pressure, and provide an additional seal above the sphincter(s). First bulb 15 can be in the form of a soft, comfortable, generally bulbous fluid chamber that can seat against and gently seal the rectal neck. First bulb 15 can include a resilient deformable shell retaining a deformable substance.

In certain embodiments, the second body or the rectal neck support described above can take the form of first bulb 15.

Grip 17 is configured to be used in inserting and removing this embodiment of the device. In use, grip 17 would remain outside the subject's anus. In an embodiment, the handle described above takes the form of grip 17.

Stem 19 is within the device providing support for outer column 11, inner column 13, bulb 15, and grip 17. In an embodiment, the shaft described above takes the form of stem 13.

Apex 21 is at the end of the device distal from the handle. Apex 21 is configured to provide a smaller diameter region of the device that can enter the anus before the wider portions of the device and make insertion more comfortable. In an embodiment, the tip described above takes the form of apex 21.

Figure 4:
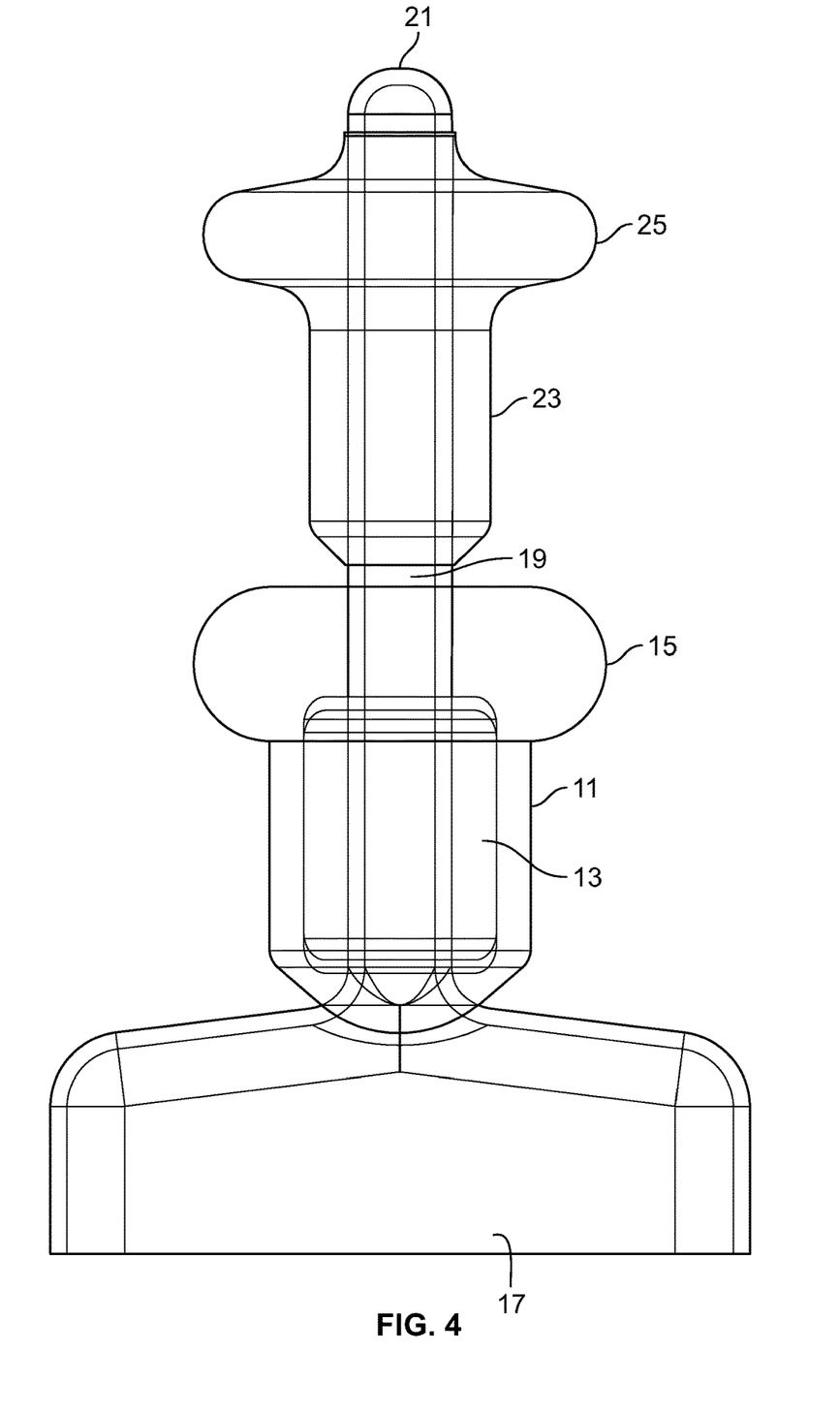
FIG. 4 schematically illustrates an embodiment of the present device.

FIG. 4 schematically illustrate an embodiment of the present device including outer column 11, inner column 13, bulb 15, grip 17, stem 19, apex 21, distal column 23, and second bulb 25. Distal column 23 and second bulb 25 form a resilient structure that can, when the device is inserted in a subject, be positioned near the Houston valves. Distal column 23 and second bulb 25 can be envisioned as providing additional blockage in the Houston valve region of the rectum. Distal column 23 and second bulb 25 can be in the form of a soft, fluid filled chamber. Distal column 23 and second bulb 25 can be configured to be positioned near or contacting one or more of the Houston valves (in the rectum) when inserted in a subject. Distal column 23 and second bulb 25 can include a resilient deformable shell retaining a deformable substance.

In certain embodiments, the third body or the Houston valve support described above can take the form of distal column 23 and second bulb 25.

Figure 5:
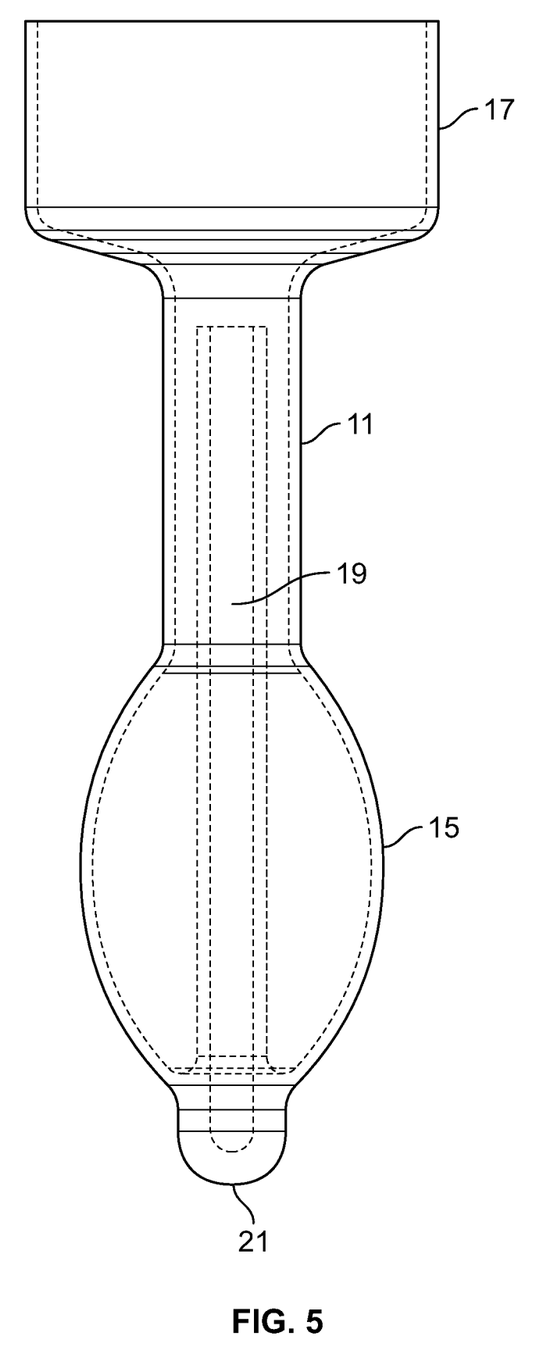
FIG. 5 schematically illustrates an embodiment of the present device.

FIG. 5 schematically illustrates an embodiment of the present device including outer column 11, first bulb 15, grip 17, stem 19, and apex 21.

Outer column 11 is a resilient structure that can, when the device is inserted in a subject, be positioned near the anal sphincter(s) to provide a seal that reduces or eliminates leakage of fecal matter, thus managing fecal incontinence. Outer column 11 can be made of a soft, deformable material against which one or both of the sphincters can depress and form a seal. Outer column 11 can be a soft and deformable portion of the device that is encircled by the sphincter muscles. In an embodiment, outer column 11 can provide a soft, pliable, generally cylindrical substrate along which the sphincter muscles can compress to form a seal for prevention of fecal leakage. This portion of the device can be made up of or include a cylinder of fluid encased within a thin, deformable elastomeric skin. Outer column 11 can be sufficiently conformable or pliable that pressure from anal sphincter(s) can cause it to conform to the shape of the tissue of the sphincter(s) or near the sphincter(s). Outer column 11 can be configured to conform to and support a subject's anal sphincter(s).

In an embodiment, the external body described above can take the form of outer column 11.

In the embodiment illustrated in FIG. 5, stem 19 can provide certain features of inner column 13, which is not present as a separate structure in this embodiment. In this embodiment, stem 19 can be configured to provide support to outer column 11, so that the device does not collapse under pressure from the anal sphincter(s). Stem 19 is less resilient than outer column 11. Stem 19 can provide sufficient support that the device can push back against the sphincter tissue to provide a seal and allow the device to be retained within the subject's anal canal.

First bulb 15 is a resilient structure that can, when the device is inserted in a subject, be positioned near the rectal neck (a widening in the anal canal) to provide an additional seal that reduces or eliminates leakage of fecal matter, thus managing fecal incontinence. In an embodiment, first bulb 15 can seat in the rectal neck, diffuse pressure, and provide an additional seal above the sphincter(s). First bulb 15 can be in the form of a soft, comfortable, generally bulbous fluid chamber that can seat against and gently seal the rectal neck. First bulb 15 can include a resilient deformable shell retaining a deformable substance.

In certain embodiments, the second body or the rectal neck support described above can take the form of first bulb 15.

Grip 17 is configured to be used in inserting and removing this embodiment of the device. In use, grip 17 would remain outside the subject's anus. In an embodiment, the handle described above takes the form of grip 17.

Stem 19 is within the device providing support for outer column 11, bulb 15, and grip 17. In an embodiment, the shaft described above takes the form of stem 13.

Apex 21 is at the end of the device distal from the handle. Apex 21 is configured to provide a smaller diameter region of the device that can enter the anus before the wider portions of the device and make insertion more comfortable. In an embodiment, the tip described above takes the form of apex 21.

Figure 6A:
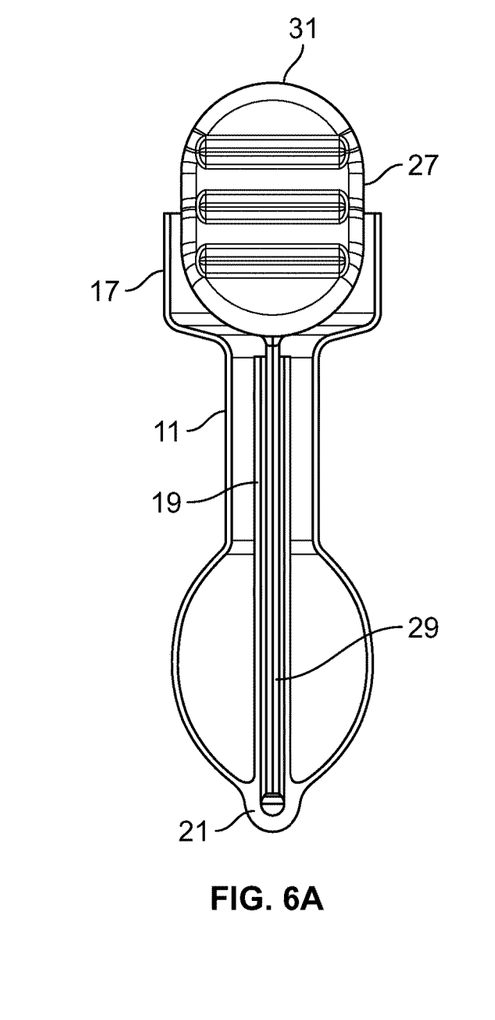
FIG. 6A schematically illustrates an embodiment of the present device.
Figure 6B:
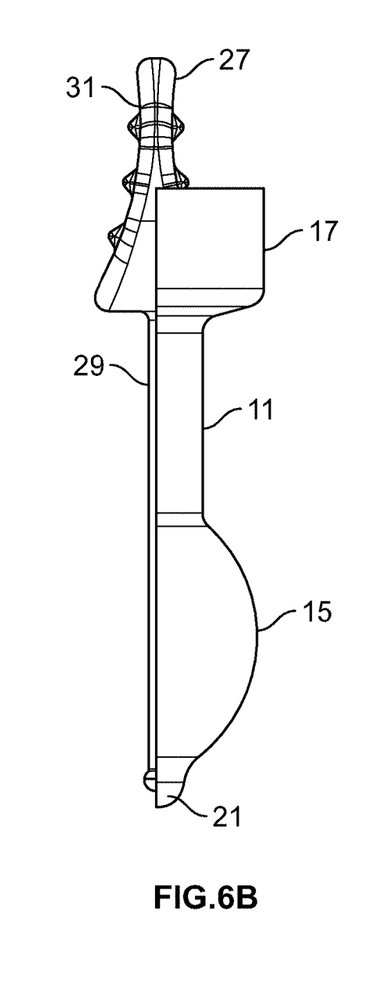
FIG. 6B schematically illustrates an embodiment of the present device.

FIG. 6 shows a cutaway view of the embodiment of FIG. 5 and including stylet 27, which is an embodiment of the applicator described above. In the illustrated embodiment, stylet 27 includes rod 29 and loop 31. Stylet 27 can be used for inserting the device into the subject then removed from the device. In the illustrated embodiment, the stylet 27 is within the device in a manner in which the tip of the shaft of the device is seated on the tip of the applicator and the handle of the device is seated against the loop 31 of stylet 27.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the term "configured" describes a system, apparatus, or other structure that is constructed or configured to perform a particular task or adopt a particular configuration. The term "configured" can be used interchangeably with other similar phrases such as arranged and configured, constructed and arranged, adapted and configured, adapted, constructed, manufactured and arranged, and the like.

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

We claim:

1. A fecal incontinence control device, comprising:
a sphincter support, the sphincter support including:
a body having an elastomeric skin containing a substance, the body including:
a first portion including a bulbous chamber containing a first portion of the substance;
a second portion including a sphincter support chamber in fluid communication with the bulbous chamber and containing a second portion of the substance; and
a grip that is wider than the second portion and widens as it extends from an end of the sphincter support chamber in a direction away from the first portion,
wherein the body is sized and configured to be inserted through a distended, loose, or patulous anal canal of a subject such that the first portion seats against a rectal neck of the anal canal to provide a seal at the rectal neck and such that the second portion resides in the distended, loose, or patulous anal canal, the second portion of the body being sized and configured to conform or deform under pressure of sphincter muscles against the skin of the second portion of the body such that the skin of the second portion of the body is configured to seal the distended, loose, or patulous anal canal to manage fecal leakage; and
wherein the grip is sized and configured to be gripped exterior to the subject when the first portion is seated against the rectal neck.

2. The device of claim 1, wherein the substance includes at least one of a liquid, a gel, or a closed cell foam.

3. The device of claim 1, wherein the second portion is cylindrical.

4. The device of claim 1, wherein the body further comprises a shaft, the first portion and the second portion being radially disposed around the shaft.

5. The device of claim 4, further comprising a stylet configured to be removably inserted into the shaft.

6. The device of claim 1, wherein the body includes a tip extending from the first body in a direction away from the second body.

7. The device of claim 1, wherein the skin includes one of silicone rubber or latex.

8. The device of claim 1, wherein the substance includes at least one of mineral oil, petrolatum, or glycerin.

9. A fecal incontinence control device, comprising:
a sphincter support, the sphincter support including:
a body having an elastomeric skin defining an encased volume containing a substance, the substance including at least one of a liquid, a gel, or a closed cell foam, the body including:
a first portion including a bulbous chamber;
a second portion including a sphincter support chamber in fluid communication with the bulbous chamber;
a grip that is wider than the second portion and widens as it extends from an end of the sphincter support chamber in a direction away from the first portion;
a shaft, the first portion and the second portion being radially disposed around the shaft; and
a tip extending from the first portion in a direction away from the second portion; and
a stylet configured to be removably inserted into the shaft,
wherein the body is sized and configured to be inserted through a distended, loose, or patulous anal canal of a subject such that the first portion seats against a rectal neck of the anal canal to provide a seal at the rectal neck and such that the second portion resides in the distended, loose, or patulous anal canal, the second portion of the body being sized and configured to conform or deform under pressure of sphincter muscles against the skin of the second portion of the body such that the skin of the second portion of the body is configured to seal the distended, loose, or patulous anal canal to manage fecal leakage; and
wherein the grip is sized and configured to be gripped exterior to the subject when the first portion is seated against the rectal neck.

10. The device of claim 9, wherein the second portion is cylindrical.

11. A method of managing fecal incontinence, comprising:
inserting the device of claim 1 into the subject.

12. A method of managing fecal incontinence, comprising:
inserting the device of claim 9 into the subject.

13. A method, comprising:
providing a fecal incontinence control device including a body having an elastomeric skin defining an encased volume containing a substance, the body including:
a first portion including a bulbous chamber; and
a second portion including a sphincter support chamber; and
inserting the device into a distended, loose, or patulous anal canal of a subject, the inserting causing passage of the substance between the bulbous chamber and the sphincter support chamber, the inserting causing the first portion to seat against a rectal neck of the anal canal, the inserting further causing the second portion to reside in the distended, loose, or patulous anal canal.

14. The method of claim 13, further comprising, subsequent to the inserting:
applying pressure of sphincter muscles of the subject against the skin of the second portion to conform or deform the second portion to seal the distended, loose, or patulous anal canal.

15. The method of claim 13, wherein the inserting causes a grip of the body to remain exterior to the subject.

16. The method of claim 15, further comprising using the grip to remove the device from the subject.

17. The method of claim 13, wherein the inserting is performed using a stylet positioned in a shaft of the body, the shaft being radially surrounded by the first portion and the second portion.

18. The method of claim 17, further comprising, subsequent to the inserting:
removing the stylet from the shaft.

19. The method of claim 13, wherein the substance includes at least one of a liquid, a gel, or a closed cell foam.

* * * * *